US010857360B2

(12) United States Patent
Waclawik

(10) Patent No.: US 10,857,360 B2
(45) Date of Patent: Dec. 8, 2020

(54) CRANIAL ELECTROTHERAPY STIMULATOR

(71) Applicant: Bart Waclawik, Carmel, IN (US)

(72) Inventor: Bart Waclawik, Carmel, IN (US)

(73) Assignee: Innovative Neurological Devices LLC, Carmel, IN (US)

( * ) Notice: Subject to any disclaimer, the term of this patent is extended or adjusted under 35 U.S.C. 154(b) by 0 days.

(21) Appl. No.: 16/270,285

(22) Filed: Feb. 7, 2019

(65) Prior Publication Data
US 2020/0009383 A1 Jan. 9, 2020

Related U.S. Application Data

(60) Provisional application No. 62/627,975, filed on Feb. 8, 2018.

(51) Int. Cl.
*A61N 1/36* (2006.01)
*H04R 1/10* (2006.01)
*H04R 3/12* (2006.01)
*A61N 1/04* (2006.01)
*G16H 20/30* (2018.01)
(Continued)

(52) U.S. Cl.
CPC ....... *A61N 1/36034* (2017.08); *A61N 1/0456* (2013.01); *A61N 1/0472* (2013.01);
(Continued)

(58) Field of Classification Search
CPC ................ A61N 1/0456; A61N 1/0472; A61N 1/36021; A61N 1/36025; A61N 1/36034;
(Continued)

(56) References Cited

U.S. PATENT DOCUMENTS 8,457,765 B2 6/2013 Kirsch et al.
8,612,008 B2 12/2013 Kirsch et al.
(Continued)

FOREIGN PATENT DOCUMENTS

CN 105749420 A 7/2016

OTHER PUBLICATIONS

English Abstract of CN105749420 A obtained from Lexis-Nexis Total Patent on Apr. 26, 2019.
(Continued)

*Primary Examiner* — George Manuel
(74) *Attorney, Agent, or Firm* — Woodard Emhardt Henry Reeves & Wagner LLP

(57) ABSTRACT

Among other things, there is disclosed a Cranial Electrotherapy Stimulator system. The system includes an electronic unit that produces low-level constant current ranging from 50 μA-500 μA that is delivered to the patient via a pair of conductive electrodes incorporated into ear cushions of a headset with a second independent wireless connection for audio purposes. The CES controls are accomplished via a smart device (phone, tablet, etc.) via a wireless protocol. The smart device contains a dedicated software application (app) that controls operation of the system, allows a user to adjust duration and intensity level of treatment, records treatment parameters (duration, intensity, frequency), presets control and customization of the presets as well as varies level, frequency and waveform shape of the current, gathers patient treatment feedback at the conclusion of each treatment, allows a patient to set up treatment reminders, and allows patient ability to store and share treatment data.

9 Claims, 14 Drawing Sheets

(51) Int. Cl.
*G16H 40/63* (2018.01)
*H04R 1/08* (2006.01)

(52) U.S. Cl.
CPC .............. *G16H 20/30* (2018.01); *G16H 40/63* (2018.01); *H04R 1/08* (2013.01); *H04R 1/1008* (2013.01); *H04R 1/1025* (2013.01); *H04R 1/1033* (2013.01); *H04R 1/1041* (2013.01); *H04R 3/12* (2013.01); *A61N 1/36021* (2013.01); *A61N 1/36025* (2013.01); *H04R 2420/07* (2013.01)

(58) Field of Classification Search
CPC ........ G16H 20/30; G16H 40/63; H04R 1/028; H04R 1/08; H04R 1/1008; H04R 1/1025; H04R 1/1033; H04R 1/1041; H04R 1/1083; H04R 2420/07; H04R 2460/01; H04R 3/12
See application file for complete search history.

(56) References Cited

U.S. PATENT DOCUMENTS

| | | |
|---|---|---|
| 2010/0145136 A1 | 4/2010 | Kirsch et al. |
| 2011/0208257 A1 | 8/2011 | Labuschagne |
| 2012/0171976 A1* | 7/2012 | Caimi ...................... H04B 1/18 |
| | | 455/193.1 |
| 2014/0277323 A1 | 9/2014 | Tingey et al. |
| 2015/0258327 A1 | 9/2015 | Chao et al. |
| 2017/0043160 A1* | 2/2017 | Goodall ................. G16H 20/30 |
| 2017/0339484 A1 | 11/2017 | Kim |
| 2017/0368329 A1* | 12/2017 | Tyler .................. A61N 1/36036 |
| 2019/0009101 A1 | 1/2019 | Neuwirth |

OTHER PUBLICATIONS

International Application No. PCT/US2019/034786 International Search Report and Written Opinion, dated Aug. 16, 2019, pp. 15.

* cited by examiner

| Date | Intensity | Freq | Start | Duration |
|---|---|---|---|---|
| 2019.01.16 | 4 | 100Hz | 01:14PM | 5MIN |
| 2019.01.03 | 4 | 100Hz | 12:32PM | 22MIN |
| 2018.12.18 | 3 | 100Hz | 10:10AM | 6MIN |
| 2018.12.06 | 3 | 100Hz | 02:14PM | 30MIN |
| 2018.12.05 | 4 | 100Hz | 04:57PM | 14MIN |
| 2018.12.04 | 4 | 100Hz | 09:54AM | 1MIN |
| 2018.12.02 | 3 | 100Hz | 09:48AM | 19MIN |
| 2018.10.28 | 4 | 100Hz | 12:37PM | 30MIN |
| 2018.10.27 | 4 | 100Hz | 04:00PM | 26MIN |
| 2018.10.23 | 3 | 100Hz | 12:12PM | 30MIN |
| 2018.10.19 | 3 | 100Hz | 04:06PM | 28MIN |

CRANIAL ELECTROTHERAPY STIMULATOR

This application claims the benefit of U.S. Provisional Application Ser. No. 62/627,975 (filed on Feb. 8, 2018), the entirety of which is incorporated herein by reference.

BACKGROUND

Research on using Cranial Electrotherapy Stimulation ("CES") for treatment of anxiety, insomnia and depression began in the former Soviet Union in the 1950s and received attention in the United States in the 1960s when electro-medical treatments were studied for pain relief. Further research focused on cranial electro-stimulation where a pair of electrodes were placed bilaterally across patient's cranium and a low-voltage (<12V DC) and low-current (<4 mA) biphasic square or quasi square-wave with frequencies ranging from <1 Hz to about 100 Hz was applied.

The electrodes for cranial electrotherapy stimulation used in commercially-available devices are attached to the patient's earlobes (e.g. via contact patches or are clipped on), to the forehead (e.g. via conductive electrodes), or to skin in the mastoid process area (e.g. via adhesive electrodes). A typical treatment usually lasts from twenty to sixty minutes. In the United States, CES medical devices are cleared by the FDA for treatment of anxiety, insomnia, and depression.

BRIEF SUMMARY OF THE DISCLOSURE

The present disclosure concerns devices and methods for controlling pain, headache, anxiety, insomnia, substance withdrawal, and/or depression using cranial electrotherapy stimulation. In particular embodiments, an apparatus or system employs over-ear headphones or headset with conductive electrodes integrated into the ear cushions to deliver the stimulation current transcutaneously to a patient's cranium. The headset is connected to a main CES device which generates the stimulation current and provides it to the electrodes via a cable resembling a traditional audio headphone cable. The main device is sized and configured to be unobtrusive, for instance capable of being located in patient's pocket during treatment. The device is controlled wirelessly via a software application ("app") that is installed on the patient's smart device (e.g. mobile phone).

One or more of the aforementioned features make the CES apparatus or system suitable for treatment anywhere due to its inconspicuous nature (the system includes a headset that is akin to or indistinguishable from an ordinary stereo over-ear headset to a casual observer, and the main CES device is small and/or concealable). Hence, this system has the potential for much better patient comfort and compliance as it can be easily incorporated into patient's lifestyle. For example, the patient will be able to use the system during work, study, or leisure activities, and it can be used in public without raising curious looks from onlookers. Patients suffering from anxiety and depression disorders usually have a heightened sense of awareness, so the ability for a device to appear unlike a traditional medical device is important. Since anxiety attacks often happen outside of a home or other familiar environment, the patient will be able to use the system before or during an anxiety-inducing event without worrying or having the added pressure of others noticing. Since the system is controlled using a dedicated app installed on a smart device (e.g. e.g. wirelessly), and particular embodiments of the main CES device can be stored in a patient's pocket, the system operation is also inconspicuous during treatment.

In particular embodiments, the headset features a second, independent, wireless connection (e.g. Bluetooth) and a built-in microphone so the patient can listen to audio or have a cellphone conversation during treatment. Therefore, a patient using the system can establish one or two simultaneous but independent wireless connections. The first connection will be between the device and the controlling software app installed on the patient's smart device and controlling administration of CES, and the second wireless connection will be established between an audio source and the system's stereo headset. The audio source can be the same smart device that controls administration of CES, or a separate wireless-enabled device (e.g. a computer). The headset also features ANR (Active Noise Reduction) in particular embodiments, which allows patients to use the device in high-noise areas (e.g. coffee shop, airport, airplane, train).

In addition to controlling the CES device, the smart device with the software app can gather information about the treatment in certain embodiments. The information gathered can include treatment parameters and patient feedback, and it can be securely stored in a cloud server. The patient has the ability to export the treatment data that can be shared with his or her health provider providing valuable clinical insight that can be used to further the treatment plan and improve clinical treatment outcomes. The app also can feature provisions for the patient to set treatment reminders, and an ability for the patient to annotate each treatment with comments which will further aid the patient's treatment provider with improving the patient's treatment plan.

Thus, among other things there is disclosed a Cranial Electrotherapy Stimulator system including in one embodiment a stereo headset with integrated dual treatment electrodes making contact on a patient's skin in the left and right mastoid process area during use. A main CES unit is attached to the headset via an electric cord or other conductor, or completely integrated inside the body of the stereo headset (cord-free operation). A smart device app controls the system, for example via a wireless protocol such as Bluetooth. A patient can use the headset for audio listening using a separate dedicated wireless connection such as Bluetooth, or use the hands-free cellular connection while undergoing treatment. The app is used to control the CES system and also to gather information about treatment including patient feedback. The app stores patient de-identified treatment information in a secure cloud server. The patient has the ability to export the treatment data, which can be shared with his or her healthcare provider.

Figure 1:
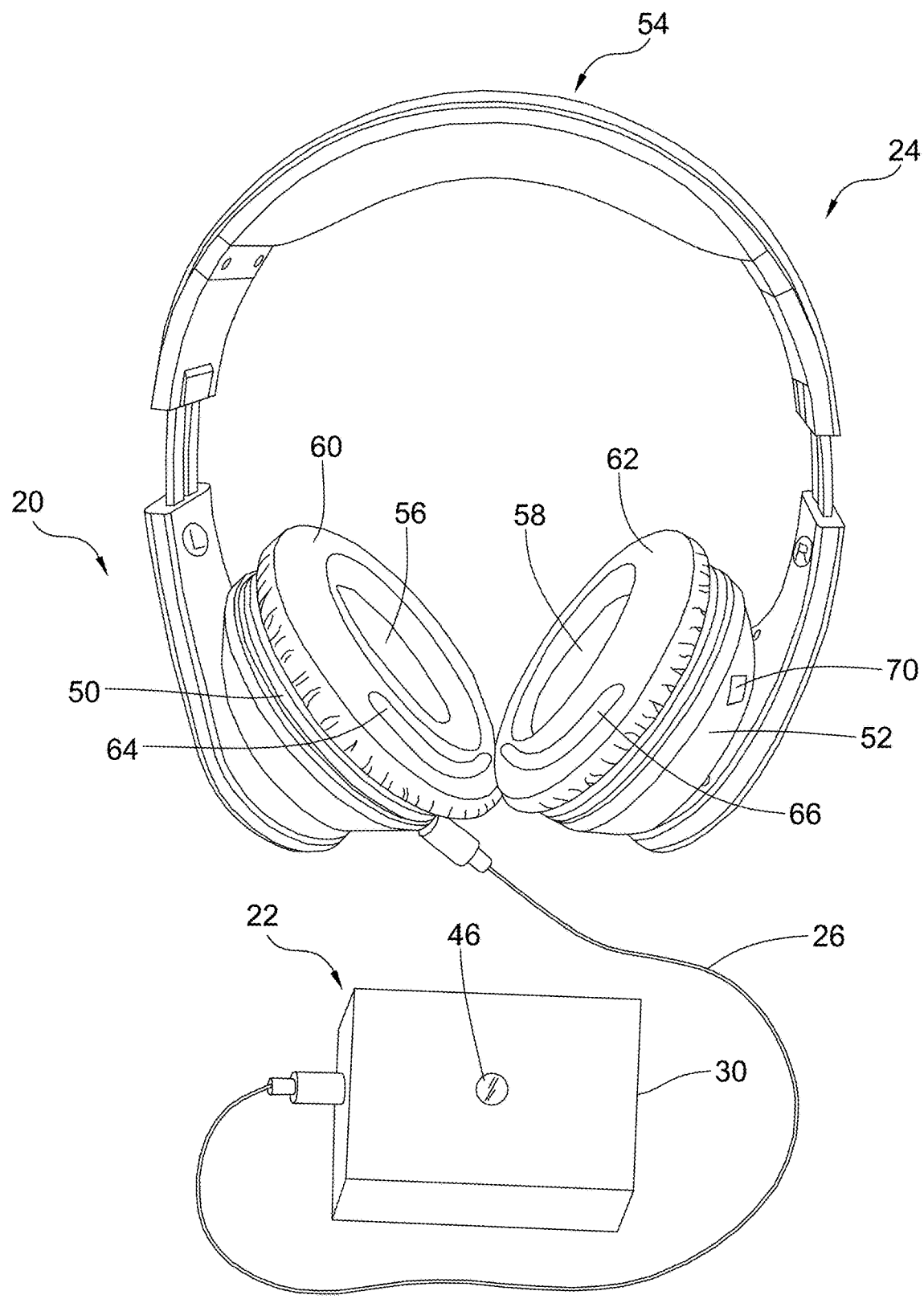
FIG. 1 is a plan view of a system for CES including a stereo headset, a control unit and a cable connecting them.

DETAILED DESCRIPTION OF THE
ILLUSTRATED EMBODIMENTS

For the purposes of promoting an understanding of the principles of the disclosure, reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates. In several figures, where there are the same or similar elements, those elements are designated with the same or similar reference numerals.

A Cranial Electrotherapy Stimulator is an electronic device that delivers low voltage (≤12 VDC) and low current (≤4 mA) impulses of electricity through the brain via two electrodes applied bilaterally across the cranium. The two electrodes are placed on the mastoid process and the signal is a biphasic square or quasi-square wave. CES devices are FDA-cleared for treatment of insomnia, depression, and anxiety.

Referring now generally to the drawings, there is shown an embodiment of a system 20 for applying CES. This embodiment of system 20 includes a main or control unit 22, a headset or headphones 24, and a cable or other electrical connector 26 that connects main unit 22 and headset 24. As discussed further below, the system may be operated via a smart device (e.g. phone or a tablet), and it may communicate with the smart device via a wireless protocol such as Bluetooth.

Main unit 22 includes a housing or enclosure 30 that includes an upper enclosure portion 32 and a lower enclosure portion 34. Portions 32 and 34 mate in any known fashion, as by snap-fit, by adhesive, mechanical connection such as one or more screws, or other manner. Within housing 30 is a circuit board 36 which includes circuitry for controlling application of currents for CES and for wireless communication with a smart device, a rechargeable battery 38, a charging port 40, a port 42 for connector 26 (directly or indirectly), a visual indicator 44 (which may be a light-emitting diode). A circular window 46 in housing 30 (e.g. in the middle of upper enclosure portion 32) allows a user to observe indicator 44, which provides device status or error conditions to the user via multi-color LED or other status display.

The illustrated embodiment of headset 24 includes first and second ear cups 50, 52 joined by a band or frame 54, which may be adjustable so as to accommodate a variety of patients. A port for connection to cable 26 may be included. Each ear cup 50, 52 includes an internal speaker 56, 58 and a padded outer rim 60, 62. Headset 24 is designed to fit over a patient's head, so that each ear cup 50, 52 fits over a respective ear of the patient, with the respective outer cushion or rim 60, 62 resting against the skin around the ear. Each rim 60, 62 includes a respective electrode 64, 66 that are integrated into the ear cushions and exposed from the respective outer surfaces of the cushions. The electrodes 64, 66 are positioned so that when the headset is on the patient's head and the patient's ears are in the ear cups, the electrodes contact at least the mastoid area of the patient (i.e. the skin area behind the patient's ears).

In particular embodiments, electrodes 64, 66, which are made of conductive fabric or other suitable conductive material, make physical contact around the entire perimeter of the respective ear cushion 60, 62 but make the electrical contact only to the mastoid process behind patient's left and right ears. This may be done by electrically isolating the area of the electrode that is not to make electrical connection and only making the section of the electrode around the mastoid area electrically active, or lowering the effective resistance of the area in the electrical contact with the mastoid area by incorporating conductive fluid at the electrode/mastoid interface. The conductive electrode material may be a silver-plated biocompatible cloth that is approved for medical applications for patient skin contact. In order to improve the electrical conductivity between the electrode and the patient skin at the mastoid interface area, a water-based gel suitable for electro-conductive applications may be applied to the skin, the electrodes, or both. In absence of electro-conductive gel, water can be used.

Figure 2:
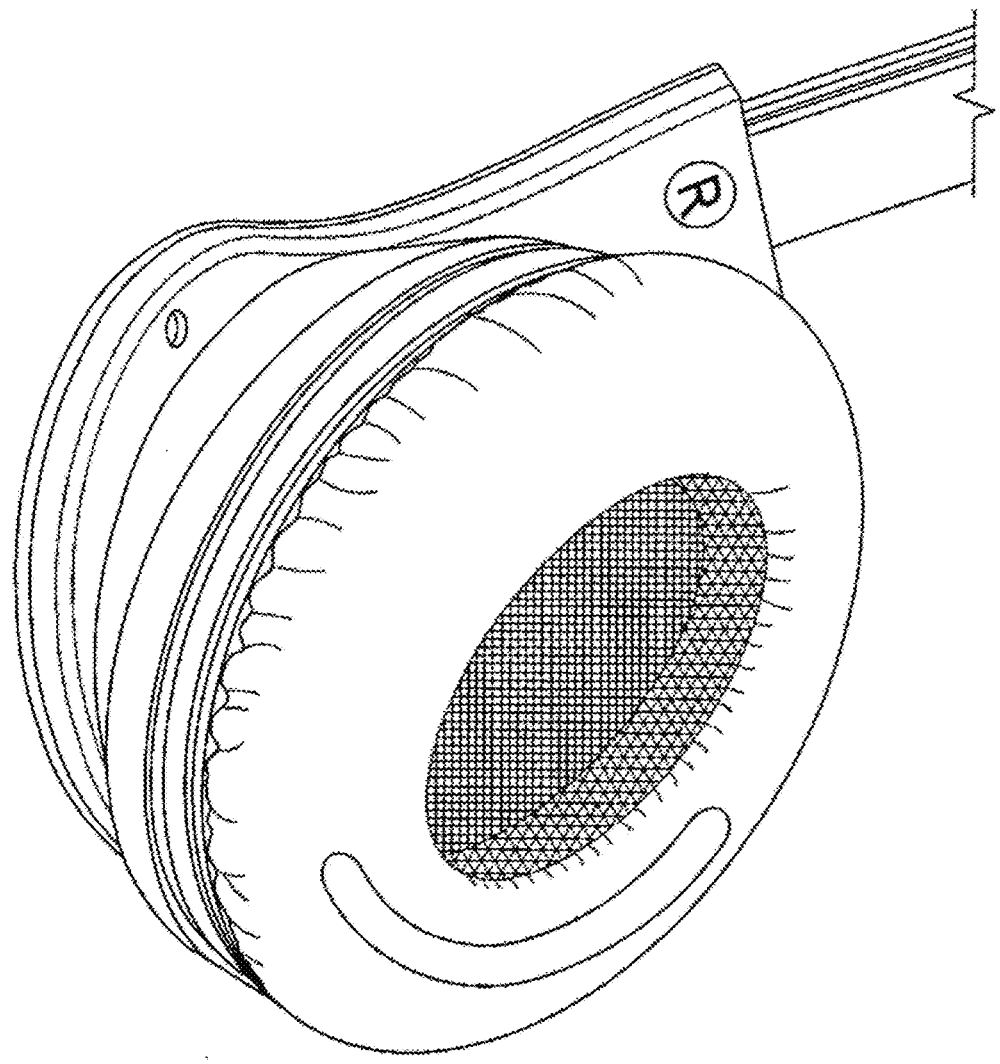
FIG. 2 is a close-up view of a portion of the headset of FIG. 1. The moon-shaped area shows the location of electrical contact (for transcutaneous treatment) between the electrode and the patient's skin around the mastoid processes behind the left and right ears
Figure 3:
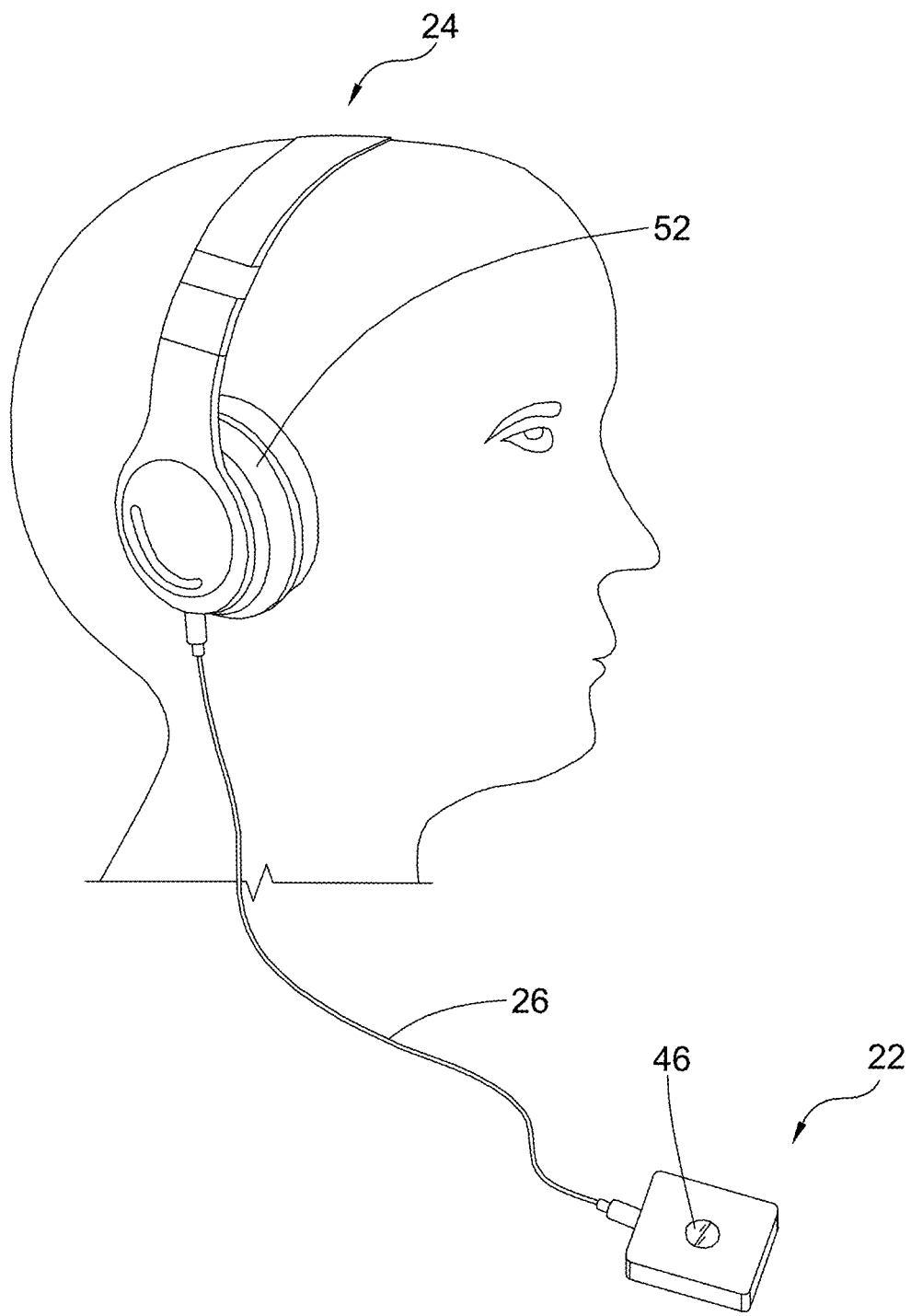
FIG. 3 is a representation of the system of FIG. 1 in use by a human patient, with electrode contact area on the skin in the location of the mastoid process(es) of the patient's head.
Figure 14:
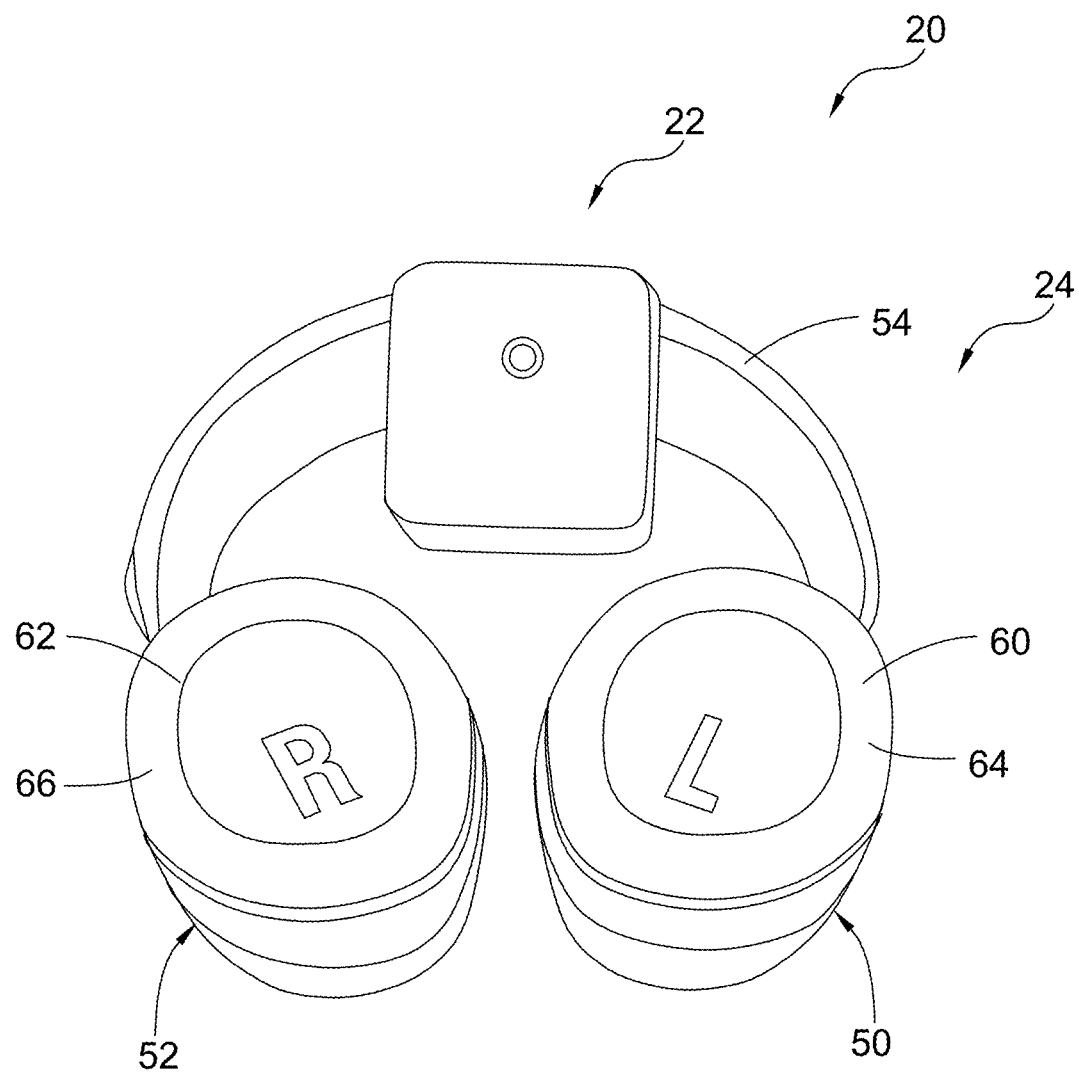
FIG. 14 is a perspective view of a system for CES including a stereo headset, and a control unit.

In particular embodiments, headset 24 features a separate wireless transceiver 70 (e.g. Bluetooth), indicated schematically in FIG. 2. A battery (e.g. a rechargeable battery) and charging or power port P (FIG. 14) may be in headset 24 to power transceiver 70 and/or other features of headset 24. Transceiver 70 allows the user to connect headset 24 and its speakers 56, 58 to an audio source using the wireless connection. The audio source can be the same device as that which houses and runs the app controlling system 20, or an independent device (e.g. laptop computer). Headset 24 may also feature an ANR (active noise reduction) component that the patient can use during the treatment. In addition, headset 24 includes a built-in rechargeable battery (not shown) that powers the ANR and wireless transceiver 70. When not in use for CES, headset 24 can be used as a standalone wireless audio headset with an ANR feature. In some embodiments, headset 24 has a built-in microphone 71 (e.g. a microphone integrated on the bottom of one of the ear cups, shown in FIG. 14) that allows the user to carry on a cellphone conversation when paired with a cellphone (e.g. via a Bluetooth or other connection through transceiver 70).

In the illustrated embodiment, headset 24 is connected to main unit via flexible cable 26. Cable 26 has suitable connections on both ends for connecting the device to headset 24 and port 42, while in other embodiments one or both ends of cable 26 may be hard-wired or otherwise connected to main unit 22 and/or headset 24. Cable 26 includes two shielded wires in a particular embodiment, one for each electrode 64,66. Electrical signals (e.g. a specified current waveform) pass from main unit 22 via cable 26 to each electrode 64, 66, as is further discussed below.

Examples of system 20 have one or more of several innovative features, which improve both the functionality and medical utility of the device, and increase patient comfort as well as patient compliance. First, system 20 incorporates conductive electrodes 64,66 into the ear cushions 60, 62 of wireless stereo over-the-ear headphones 24 with active noise reduction (ANR). A focus is on improvement of patient compliance, as the treatment can be administered during everyday tasks: work, study, and leisure activities. The ease of use and availability of entertainment or opportunity to converse by phone mean there is less chance that the patient may miss or skip the treatment due to daily schedule conflicts. Because of the inconspicuous appearance of the device, given that headset 24 when placed on the patient's head is close to or indistinguishable from standard stereo headphones, and main unit 22 is concealable in a pocket or bag, a patient can receive the treatment without worrying about curious looks from peers, coworkers or passers-by. This is especially important for adolescents who are especially vulnerable to peer pressures and are more prone to skip or forgo treatment than adults.

Figure 4:
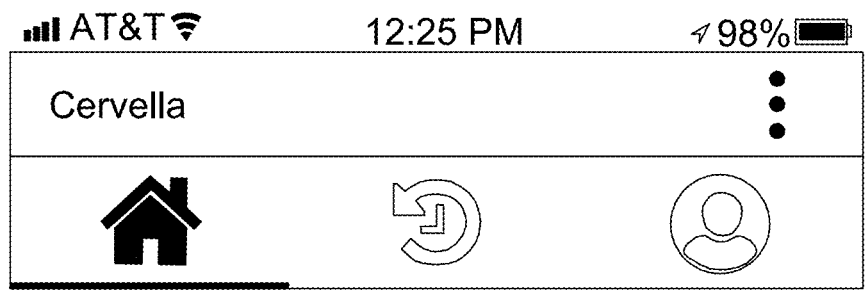
FIG. 4 is a view of an exemplary main (home) menu screen in a software app used to control the system of FIG. 1, showing for example the ability for the patient to adjust treatment intensity, frequency, duration and also to start/stop treatment. The menu also allows the patient to navigate to other menus within the software.
Figure 4:
Figure 4:
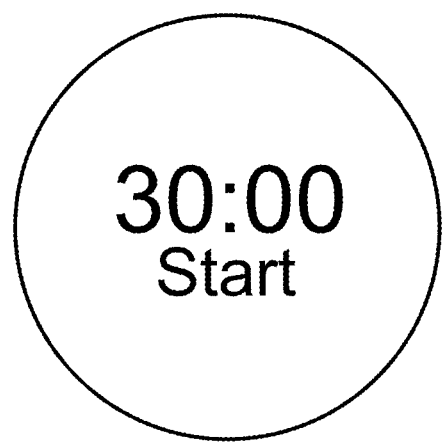

There are additional features aimed at improvement of the functionality and utility of system 20 as a medical product. First, system 20 may be controlled via an app on a smart device (FIG. 4) which allows for wireless control of system 20 via a wireless (e.g. Bluetooth) protocol. FIG. 4 shows an example of a home screen that allows the user to adjust the intensity level, e.g. from 50 μA-500 μA in 50 μA increments (10 levels). The initial level (when starting the app) is always reset to Intensity Level 1 (50 μA) in a particular embodiment. The user can also change the duration of treatment, e.g. from 10 minutes to 60 minutes with the default setting being 30 min. The user can also select from one of the pre-defined frequency settings, such as 0.5 Hz, 1.5 Hz, and 100 Hz, with the default frequency being 100 Hz. The frequency is defined as the number of current phases per second. For example, for a 100 Hz setting, a pulse consists of 100 positive phases, followed by 100 negative phases. The app is available for most common operating systems including Google Android and Apple iOS. This allows the device to send push notifications to the user's smart device (e.g. phone) providing treatment reminders.

Figure 5:
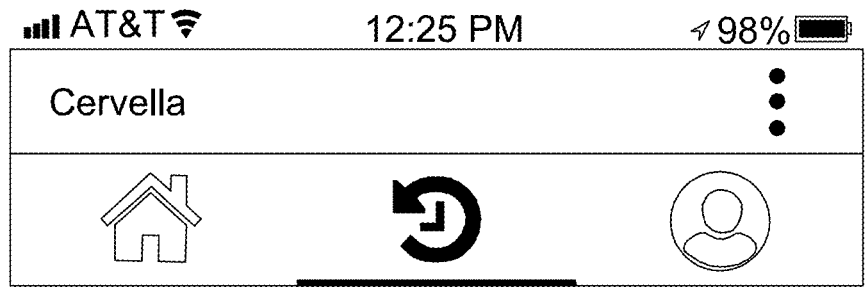
FIG. 5 is a view of a sample treatment history screen in a software app as in FIG. 4, showing treatment date, treatment intensity level, treatment frequency, start treatment time, and treatment duration.

The app may also record various treatment information applied through system 20, which may include treatment parameters (frequency and intensity level), treatment date, time, and duration, as shown in a representation of a screen in FIG. 5. The patient may be prompted to annotate his or her treatment with comments at the conclusion of each treatment for further analysis by the patient's treatment provider. Next, the app allows the patient to export the treatment data (such as that shown in FIG. 5) in a common file format (such as CSV) which can be shared by the patient with his or her physician in order to improve and further treatment. The data is stored in a patient de-identified and encrypted form in a secure cloud server. The data, in aggregate, can also be used to provide clinical insight on the effectivity of the treatment and can be used, in the aggregate, to improve the efficacy of the device. Thus, examples of an app may automatically record treatment parameter(s) such as date and time of treatment, treatment duration, frequency, and intensity, allow a patient user to annotate the treatment information with patient comments, allow a patient user to set various treatment reminders, and/or store treatment information (such as that identified above) in a de-identified form on a cloud server. The software may also be configured to allow the patient to share such data or other information with the patient's treatment or other medical provider.

Figure 6:
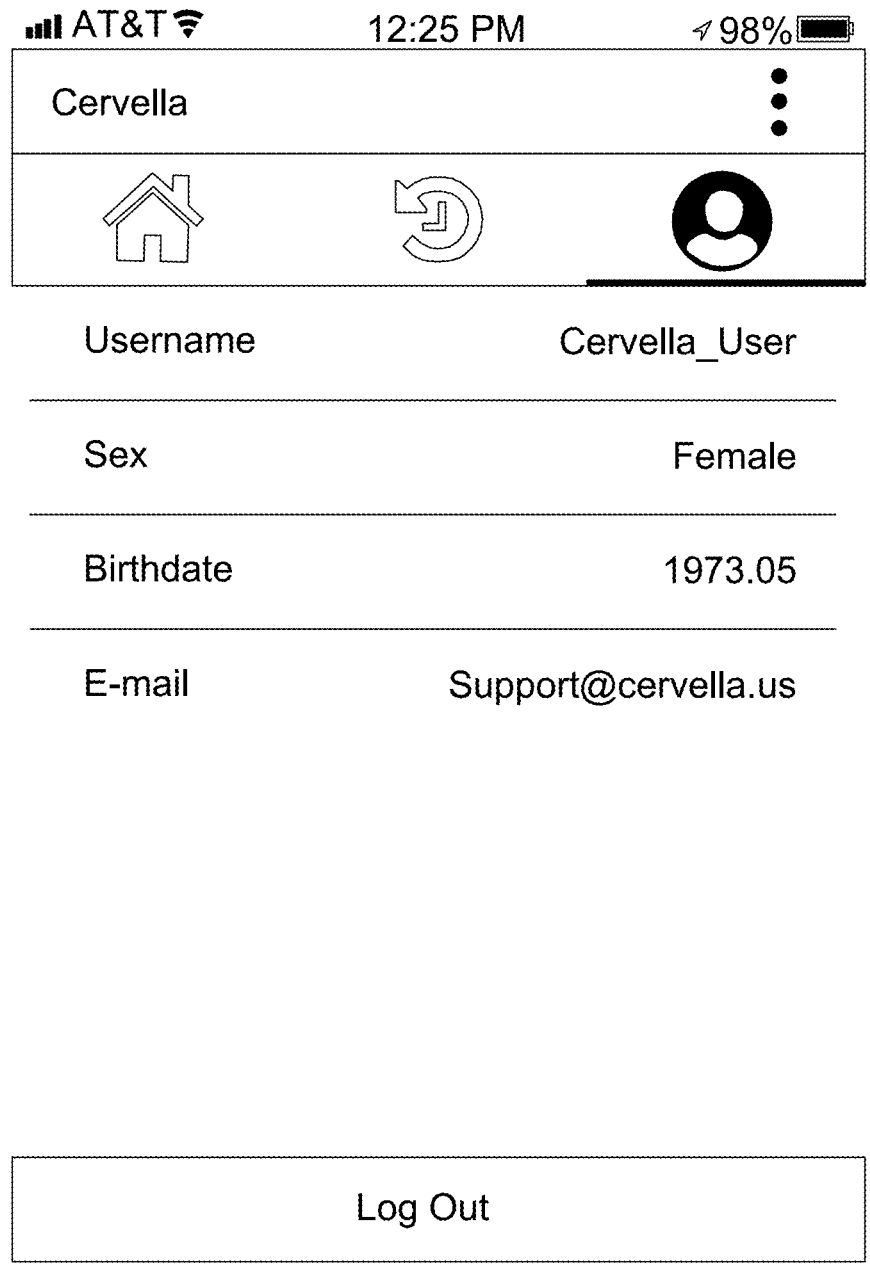
FIG. 6 is a view of a sample user account screen in a software app as in FIG. 4.

The app can be delivered to the patient via known download methods or be available on Apple Store or Google Play. The patient can be required to register so that only patients that are authorized to use the device get access to the app (e.g. as shown in FIG. 6). The app can also feature a software-as-a-service (SaaS) model allowing periodical payments from the patient or healthcare provider. The data collected from the patient is de-identified, encrypted and stored on the user's smart device as well as a cloud server.

Figure 7:
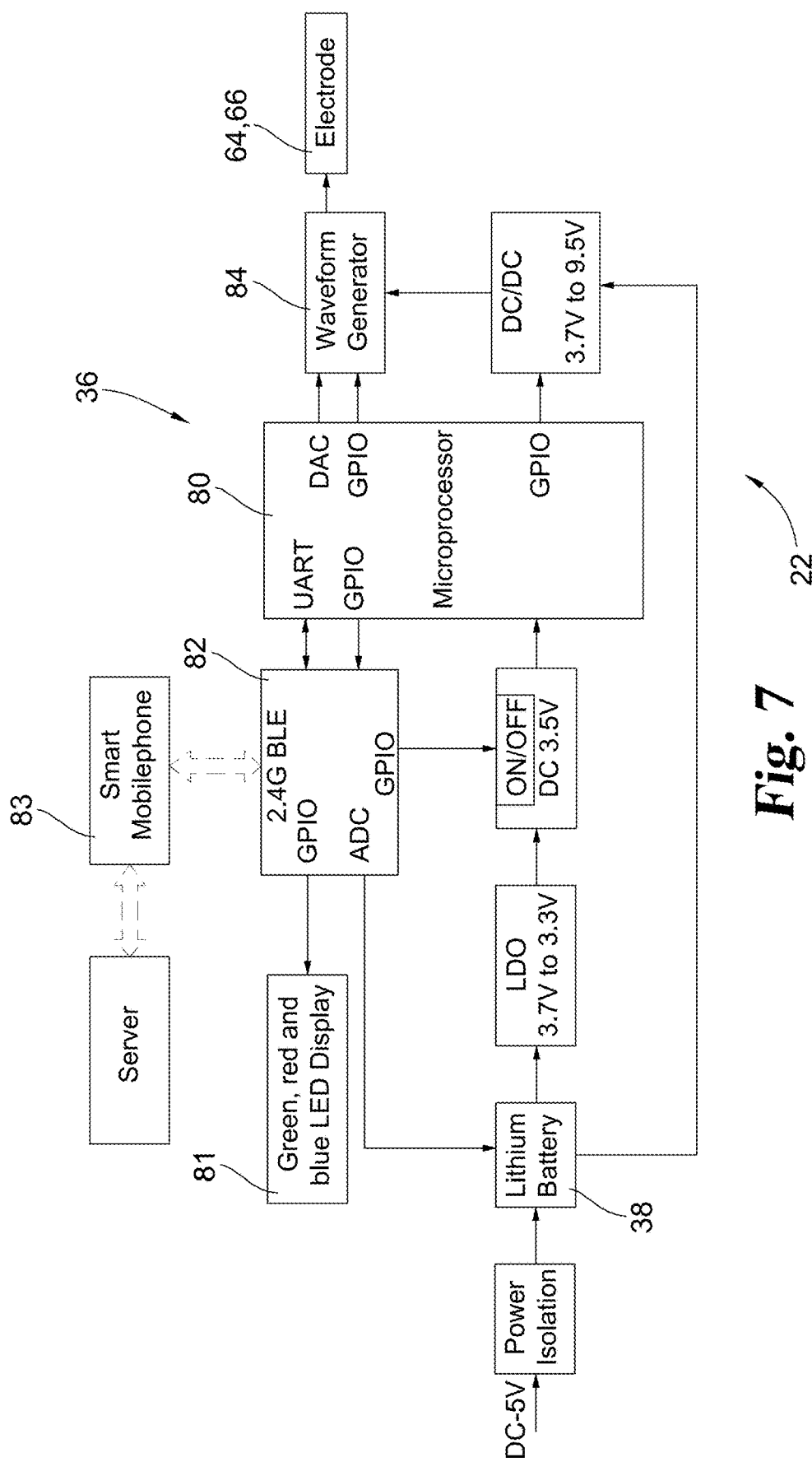
FIG. 7 is a schematic or block diagram of the system of FIG. 1.
Figure 8:
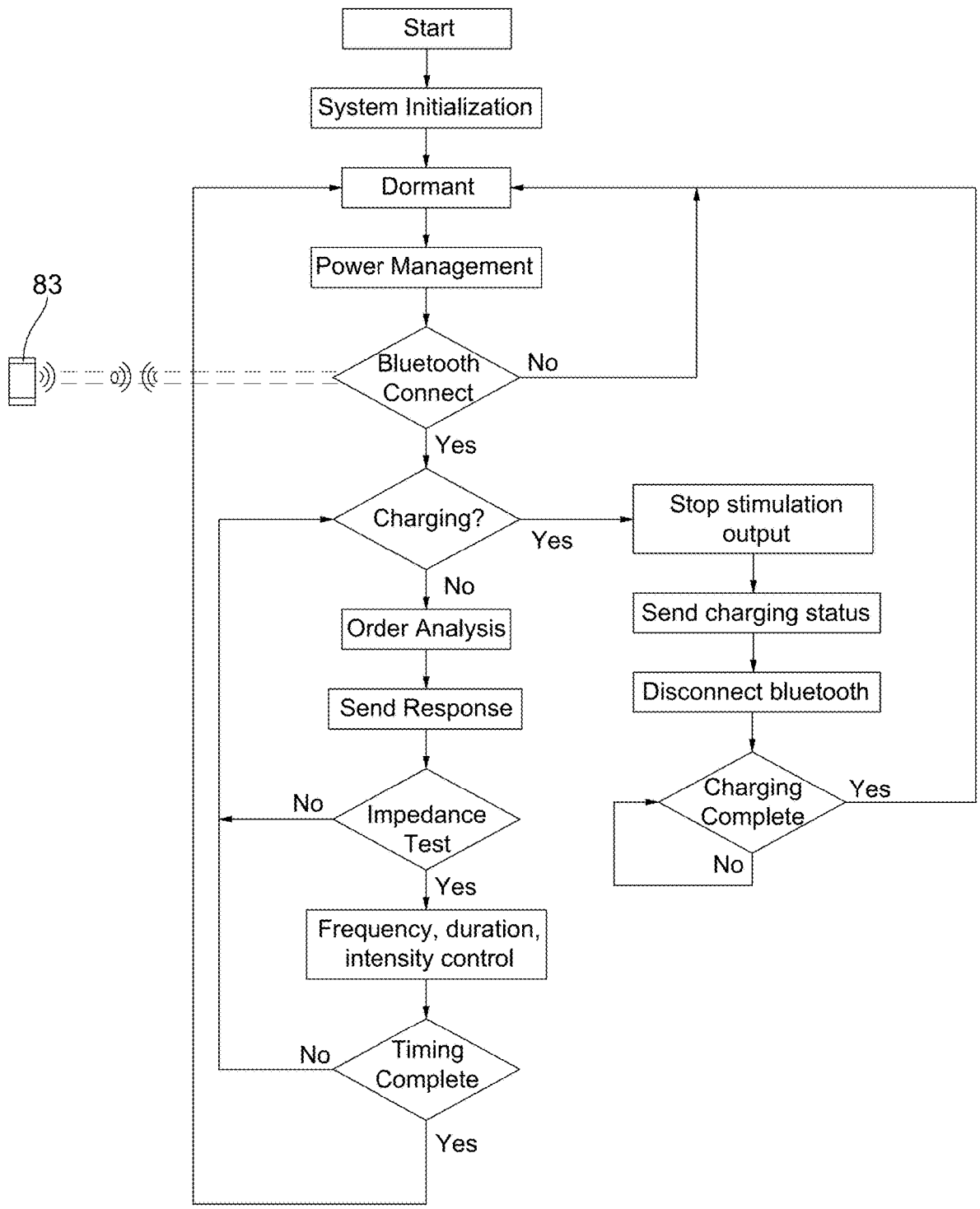
FIG. 8 is a flow chart indicating steps in operation of the system of FIG. 1.
Figure 9:
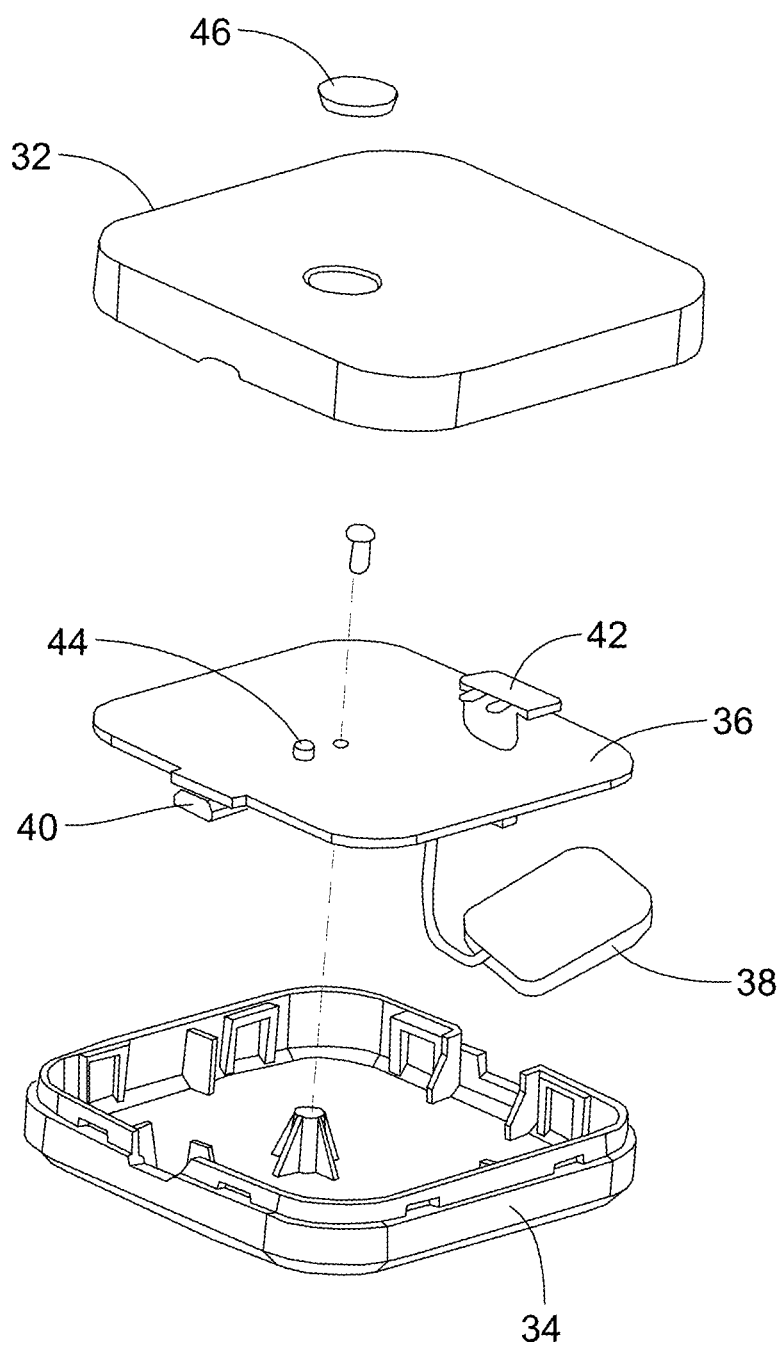
FIG. 9 is an exploded view of a portion of the system shown in FIG. 1.

System 20 is controlled by a microprocessor 80 that runs internal firmware in main unit 22, and in at least some embodiments headset 24. Microprocessor 80 communicates with transceiver 70 and a waveform generator portion of the circuitry on circuit board 36. A block diagram of system 20 is shown in FIG. 7. As discussed above, at least main unit 22 is powered by an internal, rechargeable battery 38, and headset 24 (e.g. transceiver 70) may be powered by that same battery (via a wire in cable 26, for example) or by its own battery. FIG. 8 shows a functional diagram or flow chart of system 20 in block form. FIG. 9 shows an exploded view of an embodiment of main unit 22 of system 20. Main unit 22 includes a plastic enclosure 30 meeting applicable medical device safety standards. The housing 30 features a multi-color LED indicator 81, charging port 40 and electrode connection 42. There are no on/off switches on main unit 22 in embodiments in which it is awakened by a wireless (e.g. Bluetooth) signal from the controlling application (app). Main unit 22 incorporates a wireless transceiver 82 (such as Bluetooth) that establishes a one-to-one connection with the user's smart device 83 running the controlling app. The app communicates with a cloud server through the Internet TCP/IP protocol.

Figure 10:
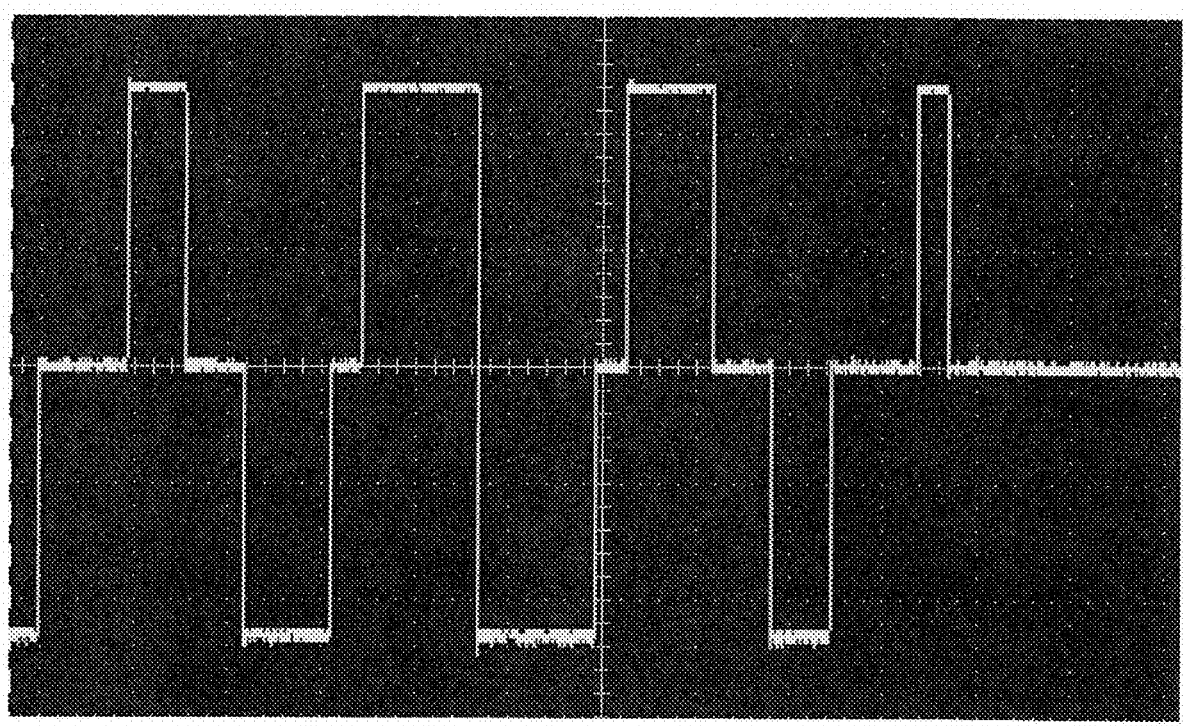
FIGS. 10-12 show typical examples of waveforms of certain frequencies usable by the system of FIG. 1 during CES, i.e. 0.5 Hz (FIG. 10), 1.5 Hz (FIG. 11), and 100 Hz (FIG. 12).
Figure 11:
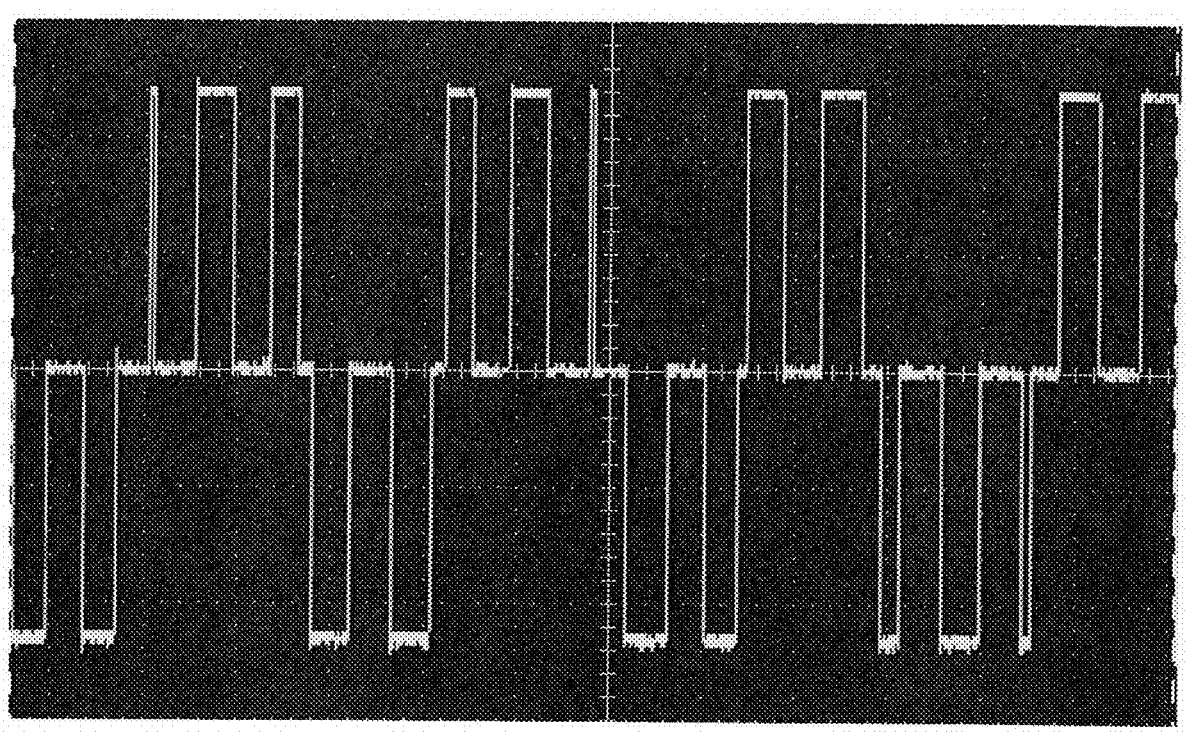
Figure 12:
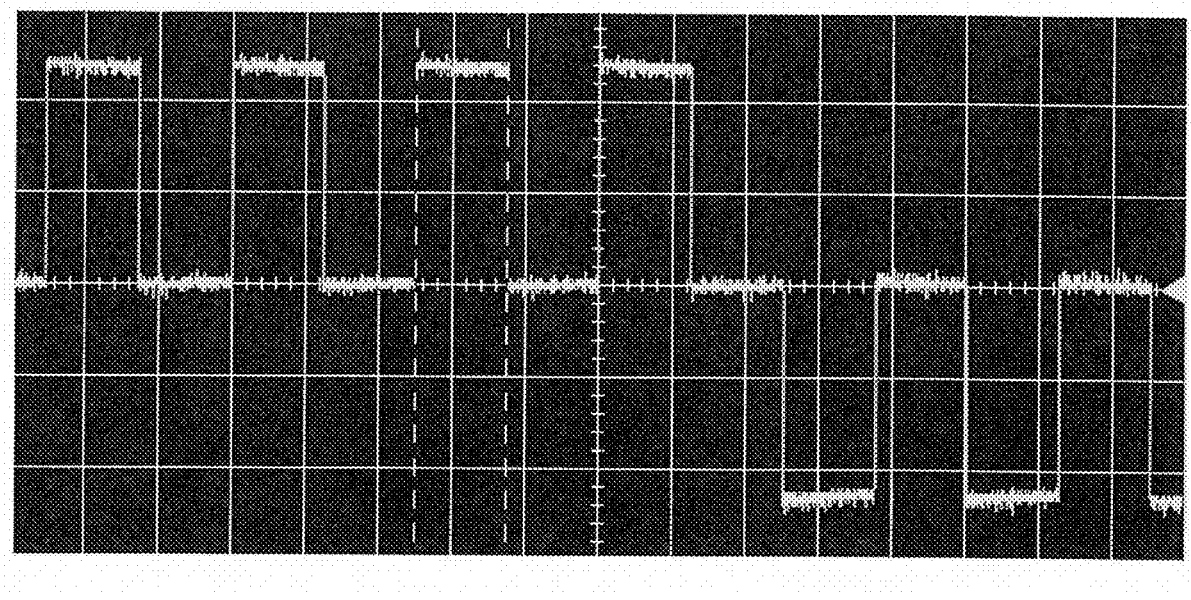

The waveform generator 84 generates quasi-square biphasic symmetrical or asymmetrical electrical waves. The amplitude of the wave varies depending on the resistance between the respective electrodes 60, 62 but typically does not exceed 10V peak-to-peak between the positive and negative phases or pulses. The duration of each phase varies between 2 ms to 1 s depending on a frequency setting. The waveform generator 84 is a constant-current circuit or device, which keeps the current flowing to electrodes 60, 62 during treatment constant per the level commanded by the user (i.e. varying the voltage applied given the resistance). An example of the waveform for the 0.5 Hz setting is shown in FIG. 10. The waveform shows positive and negative phases with various phase durations. The phase durations can vary from 250 ms to 1 s and the number of phases per second is 0.5. FIG. 11 shows an example of the 1.5 Hz waveform. The phase duration varies from 40 ms to 360 ms and the number of phases per second is 1.5. FIG. 12 shows an example of a waveform for 100 Hz. The waveform consists of a positive and negative phases with phase durations varying from 2 ms to 5 ms.

System 20 may have a provision for automatically pausing the treatment if the combined circuit resistance (combined resistance of the patient's cranium and skin) between the left and right electrodes exceeds a pre-determined resistance value (approximately 500 kΩ in one example). This can happen if a user simply removes headset 24 from his or her head during treatment or the contact patch between the electrode and skin is interrupted (e.g. the mastoid process area is blocked by hair, the skin is not clean, or the user did not position headset 24 properly on his or her head). When the user replaces headset 24 on his or her head, or adjusts the position of ear-cushions 60, 62 so that the combined circuit resistance falls below pre-determined threshold, the treatment resumes automatically.

Figure 13:
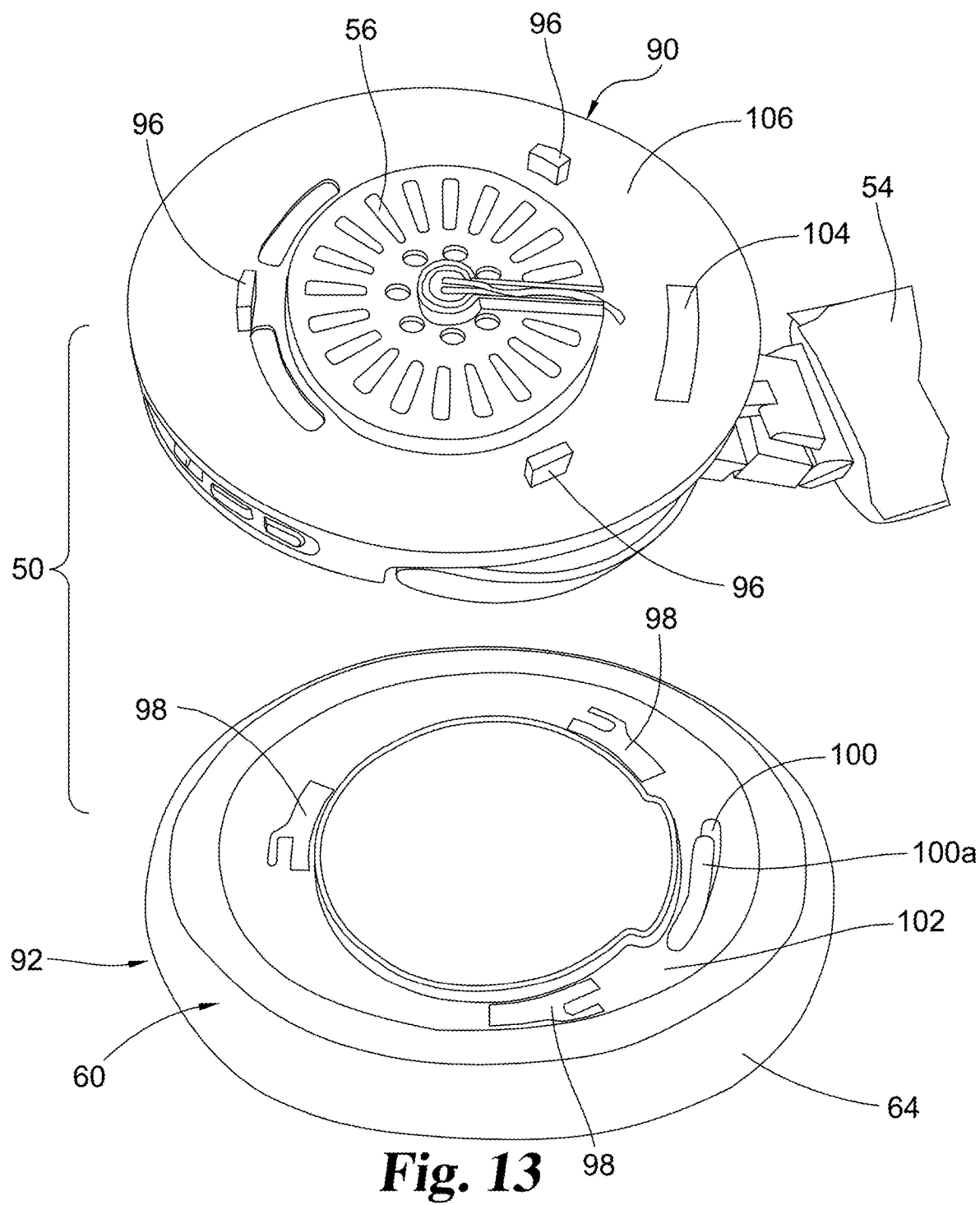
FIG. 13 is a perspective view of parts of an example of an ear cup and ear cushion with integrated electrode usable in the embodiment of FIG. 1.

In the embodiment illustrated in FIG. 13, one or both ear cups 50, 52 of headset 24 are separable, with electrical connections inside. For clarity, ear cup 50 is indicated in FIG. 13, although it will be understood that the description below could apply instead or additionally to ear cup 52. Ear cup 50 includes a base portion 90 that attaches to band or frame 54 and a detachable cushion part 92, which includes cushion 60. Cushion part 92 and base portion 90 join each other in this embodiment through a tab-and-slot arrangement, with tabs 96 on base portion 90 fitting into respective slots 98 in cushion part 92 and secured by turning cushion part 92 and base portion 90 with respect to each other. Electrode 64 is electrically connected to a contact 100 on or in the inside surface 102 of cushion part 92. A contact 104 is fixed on an inside surface 106 of base portion 90. Contact 100 as illustrated includes a portion 100a that is elevated or extending above the surface 102 of cushion part 92, and that portion 100a may be an arch (flexible or rigid), a leaf spring or similar item. Contact 104 as illustrated is a flat contact, which may also be flexible or rigid. It will be understood that an elevated contact (e.g. contact 100) may be on base portion 90 and/or a flat contact (e.g. contact 104) may be on cushion part 92 in other embodiments. When base portion 90 and cushion part 92 are fixed together, contacts 100 and 104 engage each other, e.g. with a pressing engagement from flexibility of one or both contacts, so that current can flow between them.

In this embodiment, current waveforms from main unit 22 passes to headset 24 (e.g. via cable 26) and arrives at base portion 90. It passes from base portion 90 to cushion part 92 via contacts 100, 104, and is applied to the patient by electrode 64 that is electrically connected to contact 104. One advantage in the embodiment of FIG. 13 is that such slide-on contacts allow the cushion part 92 to be easily twisted on and off for repair or replacement as necessary.

Although the disclosure has been explained in relation to particular embodiments, it is to be understood that many other possible modifications and variations can be made without departing from the spirit and scope of the disclosure. One such modification in particular, is integrating main unit 22 (i.e. the circuitry and other components within main unit 22) completely inside the enclosure of the headset 24 so that connecting cable 26 can be eliminated. The CES main device PCBA is small enough that it could easily fit inside of one of the left or right ear cups 50, 52 or cushions 60, 62. As an example, its location could be opposite of the stereo headset PCBA containing the wireless (e.g. Bluetooth) headset transceiver, rechargeable battery and ANR circuitry in order to reduce chance of interference between the two independent wireless transceivers. It is to be understood that features described with respect to one embodiment or aspect of the disclosure can be used with other embodiments or aspects of the disclosure.

What is claimed is:

1. A system for cranial electrotherapy stimulation, comprising:
 a headset adapted for placement around a patient's head for treatment, the headset having a first ear cup with a first speaker and a first outer cushion part having a first electrode fixed to the first outer cushion part, a second ear cup with a second speaker and a second outer cushion part having a second electrode fixed to the second outer cushion part, and a wireless transceiver electronically connected to the first and second speakers, wherein the first and second electrodes are positioned on their respective outer cushion parts so as to be adapted to contact skin at mastoid areas of the patient's head for transcutaneous application of current when the headset is placed for treatment; and
 a control unit electronically connected to the headset, the control unit having a housing, a circuit board and a battery within the housing, the circuit board adapted to create current waveforms with predetermined characteristics suitable for cranial electrotherapy stimulation, and to emit the current waveforms to the electrodes of the headset for a predetermined period of time,
 wherein audio can be received from an audio source by the transceiver and sent to the speakers at the same time that the current waveforms are emitted to the electrodes of the headset, so that a patient can listen to the audio during cranial electrotherapy stimulation.

2. The system of claim 1, wherein the control unit and the headset are electronically connected by a cable having at least two shielded wires.

3. The system of claim 2, wherein at least one of the control unit and the headset includes a port for connection to the cable and a recharging port.

4. The system of claim 1, wherein the control unit includes a window in the housing and a multi-color indicator reflecting status or error conditions of the control unit.

5. The system of claim 1, further comprising a microphone connected to the headset allowing a user to use the headset for telephone conversation when the headset is linked to a mobile telephone.

6. The system of claim 1, wherein the control unit includes a transceiver adapted to link to a smart device so that the control unit receives commands and/or sends data.

7. The system of claim 6, further comprising a smart device linked to the control unit via a transceiver in the control unit, wherein the smart device includes dedicated software adapted to automatically record one or more treatment parameters, allow a user to annotate treatment information with the user's comments, allow the user to set treatment reminders, and store information relating to treatment in a de-identified form on a cloud server.

8. The system of claim 7, wherein the dedicated software is adapted to allow the user to share treatment data and user comments with a medical service provider.

9. The system of claim 1, wherein the control unit is completely integrated inside the headset.

* * * * *